United States Patent [19]

Nakanishi et al.

[11] Patent Number: 5,338,874
[45] Date of Patent: Aug. 16, 1994

[54] CIS OXALATO (TRANS 1-1,2--CYCLOHEXANEDIAMINE) PT(II) HAVING OPTICALLY HIGH PURITY

[75] Inventors: Chihiro Nakanishi; Yuko Ohnishi; Junji Ohnishi; Junichi Taniuchi; Koji Okamoto; Takeshi Tozawa, all of Kanagawa, Japan

[73] Assignee: Tanaka Kikinzoku Kogyo K.K., Japan

[21] Appl. No.: 43,901

[22] Filed: Apr. 7, 1993

[30] Foreign Application Priority Data

Jan. 12, 1993 [JP] Japan ................................. 5-019508

[51] Int. Cl.$^5$ ............................................. C07F 15/00
[52] U.S. Cl. ................................................... 556/137
[58] Field of Search ........................................ 556/137

[56] References Cited

PUBLICATIONS

Kidani et al., J. Med. Chem., vol. 21, No. 12, pp. 1315–1318 (1978).

*Primary Examiner*—JoseACU G. Dees
*Assistant Examiner*—Porfirio Nazario-Gonzalez
*Attorney, Agent, or Firm*—Klauber & Jackson

[57] ABSTRACT

Disclosed herein is cis-oxalato (trans-1-1,2-cyclohexanediamine) Pt(II) optically high purity. Because of its complete optical purity, the compound is effective as raw material of such a medicine as a carcinostatic agent. The complete optical purity of the above compound may be proved by comparing the respective melting points of the cis-oxalato (trans-1-1,2-cyclohexanediamine).

2 Claims, 1 Drawing Sheet

GAS CHROMATOGRAM TRANS-dℓ-1,2-CYCLOHEXANEDIAMINE

CIS OXALATO (TRANS 1-1,2-CYCLOHEXANEDIAMINE) PT(II) HAVING OPTICALLY HIGH PURITY

BACKGROUND OF THE INVENTION

The present invention relates to cis-oxalato (trans-1-1,2-cyclohexanediamine) Pt(II) of optically high purity which can be employed as raw material of a carcinostatic agent.

While a platinum (II) complex of 1,2-cyclohexanediamine as a platinum (II) complex exhibiting a carcinostatic activity is known, the complex is a mixture of isomers synthesized from a mixture of isomers (cis, trans-d and trans-l) existing in 1,2-cyclohexanediamine the starting material thereof.

The trans and cis isomers of the 1,2 cyclohexanediamine may be optically resolved by means of a metal complex utilizing the difference of solubilities between the two isomers. For example, in Japanese patent publication No. 60-41077, while the cis-isomer is precipitated by adding a nickel (II) salt to such a nonaqueous solvent such pure methanol containing the two isomers, the trans-isomer is precipitated by adding the nickel salt and hydrochloric acid and aqueous sodium hydroxide. Since the trans-isomer of the nickel complex is slightly soluble in water and easily soluble in an organic solvent and the cis-isomer is slightly soluble in an organic solvent and easily soluble in water, the optical resolution can be conducted.

Although cis-oxalato (trans-1-1,2-cyclohexanediamine) Pt(II) was synthetically obtained through a reaction between the trans-1-1,2-cyclohexanediamine obtained in accordance with the above method and $K_2PtCl_1$ (Japanese patent publication No. 60-41077). This was also found to be the mixture with cis-oxalato (trans-d-1,2-cyclohexanediamine) Pt(II). No data are presented in the Japanese patent publication No. 60-41077 which confirm the optical purity of the cis-oxalato (trans-1-1,2-cyclohexanediamine) Pt(II) and relate to circular duchroism (CD) exhibiting its steric configuration and to an angle of rotation ($[\alpha]_D$) exhibiting its optical activity. No differences can be distinguished between their respective elemental analysis values, infrared spectra and electron spectra of the isomers mentioned in the Japanese patent publication No. 60-41077.

In the cis-oxalate (trans-1-1,2-cyclohexanediamine) Pt(II) conventionally reported, the isolation of the complex consisting of two trans-dl isomers is insufficient so that the question of the purity of the isolated Pt(II) complex remains.

Large differences in connection with a carcinostatic activity and a secondary effect between isomers of many optically active medicines, and their optical purity is especially important when they are employed as medicines.

SUMMARY OF THE INVENTION

The present invention has been made in view of this standpoint.

An object of the present invention is to provide a platinum complex compound having optically high purity.

Another object of the invention is to provide a platinum complex compound which is useful as raw material of a pharmaceutically active agent because of its high purity.

The present invention is cis-oxalato (trans-1-1,2-cyclohexanediamine) Pt(II) of optically high purity having a general formula of Formula (1).

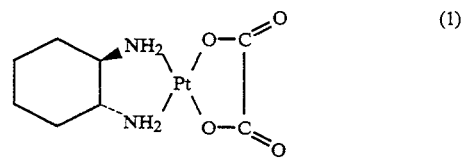

The cis-oxalato (trans-1-1,2-cyclohexanediamine) Pt(II) of optically high purity of the present invention may be prepared by completely and optically resoluting the Pt(II) optical isomers by means of a process of optically resoluting an optically active platinum complex compound disclose in an application of the same Applicant of the same date.

Since the complex compound of the present invention contains no cis-oxalato (trans-1-1,2-cyclohexanediamine) Pt(II) of optically isomer thereof, the excellent results of acute toxicity can be obtained in comparison with cis-oxalato (trans-1-1,2-cyclohexanediamine) Pt(II) conventionally obtained contaminated with an optical isomer so that it is effective for providing medicines on higher safety.

The boiling point of the cis-oxalato (trans-1-1,2-cyclohexanediamine) Pt(II) is, because of the absence of impurities, lower than of that of conventionally prepared cis-oxalato (trans-1-1,2-cyclohexanediamine) Pt(II).

DETAILED DESCRIPTION OF THE INVENTION

Figure 1:
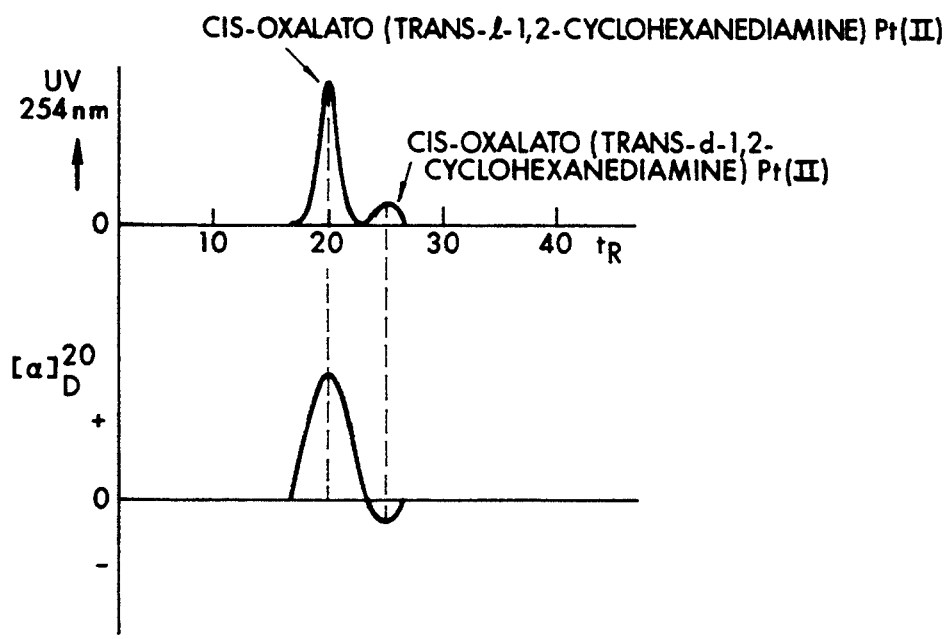
FIG. 1 is a chromatogram obtained in HPLC of cis-oxalato (trans-1-1,2-cyclohexanediamine) Pt(II) before optical obtained in Example 1, Example 2 and Example 3. The upper portion shows an amount of elution per unit time as a relative absorption amount of ultraviolet ray at 254 nm, and the lower portion 1 shows an amount of elution per unit time as a relative degree of rotation.

The cis-oxalato (trans-1-1,2-cyclohexanediamine) Pt(II) of optically high purity represented by Formula (1) of this invention may be prepared in accordance with a following illustrative method.

Commercially available 1,2-cyclohexanediamine (for instance, trans-1-1,2-cyclohexanediamine made by Aldrich, cis and trans-dl mixed 1,2-cyclohexanediamine made by Tokyo Kasei K.K.) may be employed. The compounds made by Aldrich and Wako Junyaku were employed without further treatment because of their relatively high purity, and the geometrical isomers of cis and trans that made by Tokyo Kasei may be resoluted and purified in accordance with such a known process as that disclosed in Japanese patent publication No. 61-4827. The optical resolution of the trans isomer may be conducted by forming a diastereoisomer in accordance with a normal method by means of tartaric acid and employing a recrystallization method.

A crystal of cis-dichloro(trans-1-1,2-cyclohexanediamine) Pt(II) represented in Formula 2 may be obtained by a reaction between the trans-1-1,2-cyclohexanediamine previously obtained and an equivalent weight of potassium tetrachloroplatinate [K₂PtCl₄] dissolved in water at room temperature over 10 hours.

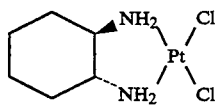
(2)

After the compound represented in Formula 2 is suspended in water followed by the addition of two equivalent weights of an aqueous solution of silver nitrate, the reaction is allowed to proceed over 24 hours in the dark followed by the removal of silver chloride by means of filtration to produce an aqueous solution of cis-diaquo(trans-1-1,2-cyclohexanediamine) Pt(II) nitrate represented in Formula 3. After potassium iodide is added to this solution followed by the removal of the excess silver ion as silver iodide by means of filtration and the decolorization and purification by active carbon, an equivalent weight of oxalic acid in respect to the potassium tetrachloroplatinate is added to produce a crude crystal of cis-oxalato(trans-1-1,2-cyclohexanediamine) Pt(II) after the two hours' reaction. Cis-oxalato(-trans-1-1,2-cyclohexanediamine) Pt(II) obtained by the recrystallization of the said crude crystal from hot water is a mixture with cis-oxalato(trans-d-1,2-cyclohexanediamine) Pt(II) which is an optical isomer thereof.

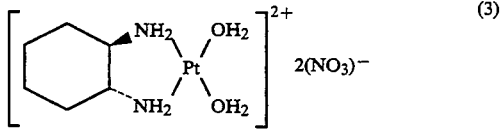
(3)

Then, the recrystallized crystal is completely isolated as cis-oxalato (trans-1-1,2-cyclohexanediamine) Pt(II) in accordance with the process of resoluting and purifying the optically active Pt(II) isomers after the crystal is dissolved in water. That is, the cis-oxalato(trans-1-1,2-cyclohexanediamine) Pt(II) contaminated with no optical isomers can be obtained by freeze-drying an aqueous solution separately eluted by means of high peformance liquid chromatography (hereinafter referred to as "HPLC"), for example, under the following conditions.

Separation column: 4.6 mm of inner diameter and 25 cm of height packed with OC of Daicel Chemical Industries, Ltd.

Mobile phase: othanol/methanol=30:70 (volume ratio)

Flow rate: 0.2 ml/min.

Column temperature: 40° C.

Detector:

ultraviolet ray 254 nm optical rotation 580 nm.

the cis-oxalato(trans-1-1,2-cyclohexanediamine) Pt(II) having the high optical purity in accordance with the present invention is active against a tumor "leukomia L1210" and effective as a carcinostatic agent.

EXAMPLES

Then, a representative process of preparing the cis-oxalato (trans-1-1,2-cyclohexanediamine) Pt(II) of this invention, its properties and biological activities will be described in Examples. Further, in fact, that compound prepared by a conventional method is a mixture of optical isomers will be shown contrary to a known fact.

EXAMPLE 1

① Preparation of cis-dlchloro(trans-1-1,2-cyclohexanodiamine) Pt(II)

A reaction between 46.8 g of trans-1-1,2-cyclohexanediamine made by Aldrich ($[\alpha]^{19}_D = -35.6°$, 4% $H_2O$) and 170 g of potassium tetrachloroplatinate (made by Tanaka Kikinzoku Kogyo K.K.) in an aqueous solution at room temperature over 10 hours yielded needles of cis-dichloro(trans-1-1,2-cyclohexanediamine) Pt(II). Yield: 99%.

② Preparation of cis-diaquo(trans-1-1,2-cyclohexanediamine) Pt(II) nirtrate

The cis-dichloro(trans-1-1,2-cyclohexanediamine) Pt(II) obtained above was suspended in 1.6 liters of water to which was added two molar volumes of silver nitrate for proceeding a reaction in the dark over 24 hours, and the silver chloride produced during the reaction was filtered off. After 4.8 g of potassium iodide was added to this filtrate followed by the precipitation of the excess silver ion as silver iodide produced during the reaction of over 12 hours, 1 g of active carbon for purification and decolorization was added which was then filtered off together with the silver iodide.

③ Preparation of cis-oxalate(trans-1-1,2-cyclohexanediamine) Pt(II)

To the filtrate obtained above was added 48 g of oxalic acid dihydrate to yield 90 g of a white crude crystal after a two hours' reaction.

Then, 80 g of this crude crystal was recrystallized from three liters of hot water, and 45 g of the obtained crystal was dissolved into 9 liters of water. HPLC was conducted employing the solution under the following conditions to obtain a chromatogram of FIG. 1.

Column for optical resolution: Column having a length of 50 cm and an inner diameter of 5 cm packed with OC (Daicel Chemical Industries, Ltd., a filler prepared by adsorbing a cellulose carbamate derivative to silica gel)

Mobile phase: ethanol/methanol=30:70 (volume ratio)

Flow rate: 2.0 ml/min.

Column temperature: 40° C.

Detection:

ultraviolet ray 254 nm optical rotation 589 nm.

The upper portion of FIG. 1 shows an amount of elution per unit time as a relative absorption amount of ultraviolet ray at 254 nm, and the lower portion of FIG. 1 shows an amount of elution per unit time as a relative degree of rotation. At a retention time ($t_R$) of 25 minutes, cis-oxalato(trans-d-1,2-cyclohexanediamine) Pt(II) was found to be contaminated. The optical purity of the cis-oxalato(trans-1-1,2-cyclohexanediamine) Pt(II) prepared by employing the trans-1-1,2-cyclohexanediamine made by Aldrich ($[\alpha]^{19}_D = -35.6°$, 4% $H_2O$) was calculated in accordance with a below equation to be 88.5% of an enantiomer excess rate (Table 1). Then, cis-oxalato(trans-1-1,2-cyclohexanediamine) Pt(II) of 100% of an optical purity (e.e.) was obtained by collecting an aqueous solution eluted in fractions from 15 minutes to 22 minutes ($t_R$) followed by freeze drying. Yield: 39.8 g 50% (based on the crude crystal).

[Equation for calculating optical purity]

Optical purity (%) ... e.e (%) =

{([content of cis-oxalato(trans-1-1,2-cyclohexanediamine) Pt(II)] −

[content of [cis-oxalato(trans-d-1,2-cyclohexanediamine) Pt(II)]])/

([content of cis-oxalato(trans-1-1,2-cyclohexanediamine) Pt(II)] +

[content of [cis-oxalato(trans-d-1,2-cyclohexanediamine) Pt(II)]])} × 100

(e.e.: enantiomer excess rate)

EXAMPLE 2

①  Resolution of cis and trans geometrical isomers

To a solution prepared by dissolving 100 g of cis, trans-dl-mixed-1,2-cyclohexanediamine into 640 ml of methanol was added a solution prepared by dissolving 104 g of nickel chloride [$NiCl_2.6H_2O$] into 1760 ml of methanol which was then reacted at room temperature for 2 hours under stirring. A precipitated yellow crystal [Ni(cis-1,2-cyclohexanediamine)$Cl_2$ (31.6 g) was filtered and washed with methanol and air-dried. To this crystal was added 140 ml of 6-normal hydrochloric acid and then its pH was adjusted to 4.2~4.5 with a 15% sodium hydroxide aqueous solution. After a precipitated royal purple crystal [Ni(trans-dl-1,2-cyclohexanediamine)-($H_2O)_2Cl_2$] (72.0 g) was filtered and washed, 120 ml of 6-normal hydrochloric acid was added thereto. It was concentrated under a reduced pressure followed by addition of 600 ml of ethanol and 600 ml of acetone to obtain colorless precipitate [trans-dl-1,2-cyclohexanediamine.2HC.] (42.54 g) after filtration which was then wased with ethanol-acetone. After this was extracted with chloroform and dried with potassium carbonate, a colorless liquid [trans-dl-1,2-cyclohexanediamine (35.5 g)] ($[\alpha]^{19}_D = 0°$, 4% $H_2O$) was obtained. A single peak appeared on a gas chromatogram at $t_R = 3.043$ minutes.

Figure 2:
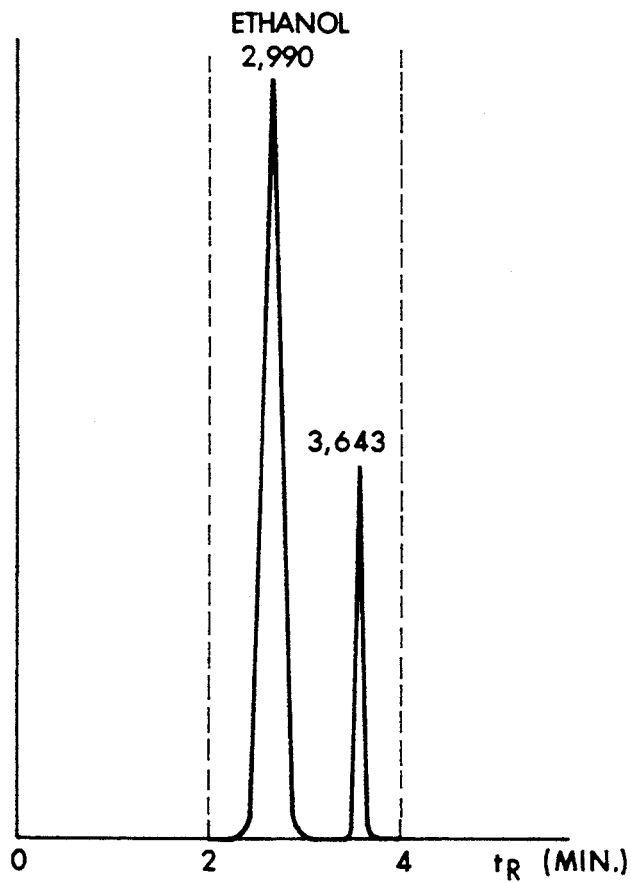
FIG. 2 is a chromatogram of trans-dl-1,2-cyclohexanediamine obtained in ① of Example 2.

FIG. 2 is a gas chromatogram of trans-dl-1,2-cyclohexanediamine.

The gas chromatography was conducted under the following conditions.

Column: CP-Cyclodextrin-B-236-M-19 50 m×0.25 mm (inner diameter) df=0.25 μm
Column temperature: 200° C.
Carrier gas: $N_2$, 2 kg/$cm^2$
Injector temperature: 200° C.
Detector: FID (200° C.)
Sample volume: 1 μl.

② Optical resolution of trans-dl-1,2-cyclohexanediamine

To 35.5 g of the trans-dl-1,2-cyclohexanediamine previously obtained was added 671 ml of water for dissolving under heating at 90° C. The standing thereof for 12 hours after the gradual addition of 22.10 g of d-tartaric acid and 13.4 ml of glacial acetic acid produced 16.23 g of a diastereoisomer (trans-1-1,2-cyclohoxanediamine (1) tartaric acid. This was recrystallized from water twice. No further change of the rotation of angle was observed after the repeated recrystallization as shown in FIG. 2.

After 9.23 g of the diastereoisomer obtained was dissolved into a small amount of water followed by the addition of 5.64 g of sodium hydroxide, it was extracted with ether and was distilled under a reduced pressure to obtain 3.20 g of a colorless liquid, trans-1-1,2-cyclohexanediamine.

③ Preparation of cis-dichloro(trans-1-1,2-cyclohexanediamine) Pt(II)

In accordance with the same procedures as those of ① of Example 1 except that the trans-1-1,2-cyclohexanediamine obtained in ② of Example 2 was employed as raw material in place of the trans-1-1,2-cyclohexanediamine made by Aldrich of ① of Example 1, 9 g of the corresponding Pt(II) complex was obtained.

④ Preparation of cis-diaquo(trans-1-1,2-cyclohexanediamine) Pt(II) nitrate

In accordance with the same procedures as those of ② of Example 1 except that the Pt(II) complex obtained in ③ of Example 2 was employed in place of cis-dichloro(trans-1-1,2-cyclohexanediamine) Pt(II) obtained in ① of Example 1, an aqueous solution of the desired Pt(II) complex was obtained.

⑤ Preparation of cis-oxalato(trans-1-1,2-cyclohexanediamine) Pt (II)

In accordance with the same procedures as those of ③ of Example 1 except that the aqueous solution of the Pt (II) complex obtained in ④ of Example 2 was employed in place of the aqueous solution of the Pt(II) complex obtained in ② of Example 1, 7 g of a crude crystal of cis-oxalato(trans-1-1,2-cyclohexancdiamine) Pt(II) was obtained. After the recrystallization of this crude crystal from hot water was conducted, 4 g of the recrystallized crystal was dissolved into 800 ml of water. Th HPLC of this solution under the same conditions of those of ③ of Example 1 revealed that cis-oxalato(trans-d-1,2-cyclohexanediamine) Pt(II) which was an optical isomer was apparently contaminated at $t_R = 25$ minutes as shown in FIG. 1.

The optical pority of the cis-oxalato(trans-1-1,2-cyclohexanediamine) Pt(II) synthesized by employing the raw material isolated in accordance with a process of resoluting and purifying isomers (Japanese patent application No. 61-4827) was e.e.=90.0% in accordance with the equations of ③ of Example 1 as shown in Table 1. Then, cis-oxalato(trans-1-1,2-cyclohexanediamine) Pt(II) of 100% of an optical purity (e.e.) was obtained by collecting an aqueous solutioneluted in fractions from 15 minutes to 22 minutes ($t_R$) followed by freeze drying. Yield: 3.6 g, 51% (based on the crude crystal).

EXAMPLE 3

① Preparation of cis-dichloro(trans-1-1,2-cyclohexanediamine) Pt(II)

In accordance with the same procedures as those of ① of Example 1 except that the trans-1-1,2-cyclohexanediamine made by Wako Junyaku K.K. ($[\alpha]^{19}_D = 34.9°$, 4% $H_2O$) was employed in place of the trans-1-1,2-cyclohexanediamine made by Aldrich of ① of Example 150 g of the corresponding Pt(II) complex was obtained.

② Preparation of cis-diaquo(trans-1-1,2-cyclohexanediamine) Pt(II) anitrate

In accordance with the same procedures as those of ② of Example 1 except that the Pt(II) complex obtained in ① of Example 3 was employed in place of cis-dichloro(trans-1-1,2-cyclohexanediamine) Pt(II) obtained in ① of Example 1, an aqueous solution of the desired cis-diaquo(trans-1-1,2-cyclohexanediamine) Pt(II) nitrate was obtained.

③ Preparation of cis-oxalato(trans-1-1,2-cyclohexanediamine) Pt(II)

In accordance with the same procedures as those of ③ of Example 1 except that the aqueous solution of the Pt(II) complex obtained in ② of Example 3 was employed in place of the aqueous solution of the Pt(II) complex obtained in ② of Example 1, 90 g of a crude crystal of cis-oxalato(trans-1-1,2-cyclohexanediamine) Pt(II) was obtained. After the recrystallization of this crude crystal from hot water was conducted, 45 g of the recrystallized crystal was dissolved into 9 liters of water. The HPLC of this solution under the same conditions of those of ③ of Example 1 revealed that cis-oxalato(trans-d-1,2-cyclohexanediamine) PT(II) which was an optical isomer was apparaently contaminated at $t_R=25$ minutes as shown in FIG. 1. The optical purity of the cis-oxalato(trans-1-1,2-cyclohexanediamine) Pt(II) synthesized by employing trans-1-1,2-cyclohexanediamine made by Wako Junyaku K.K. as raw material was e.e. = 86.8% in accordance with the equation of ③ of Example 1 as shown in Table 1. Then, cis-oxalato(trans-1-1,2 cyclohexanediamine) Pt(II) of 100% of an optical purity (e.e.) was obtained by collecting an aqueous solution eluted in fractions from 15 minutes to 22 minutes ($t_R$) followed by freeze drying. Yield: 39.1 g, 43% (based on the crude crystal).

COMPARATIVE EXAMPLE

For comparing and evaluating the optical purity, the physicochemical properties and the biological properties obtained in accordance with the present invention, the cis-oxalate(trans-1-1,2-cyclohexanediamine) Pt(II) was synthesized as Comparative Example by employing the raw material made by Tokyo Kasei K.K. in accordance with the following procedures disclosed Japanese patent publication No. 60-41077.

To 3 g of cis-dichloro(trans-1-1,2-cyclohexanediamine) Pt(II) was added 500 ml of water followed by the boiling thereof for dissolution. After two moles of $AgNo_3$ (2.6 g) were added and was stireed for 2 to 3 hours in the dark, the filtrations were repeated until the filtrate became transparent. After the filtrate was concentrated under a reduced pressure to 100 ml, 1.3 g of potassium oxalate was added to the concentrated solution followed by standing for 8 hours at room tempeature. The solution was again concentrated at a reduced pressue to produce white crystalline precipitate. The precipitated was recrystallized from water.

The comparisons of the optical purity between the cis-oxalato(trans-1-1,2-cyclohexanediamine) Pt(II) of Examples and Comparative Example, that of the physicochemical properties and that of the biological properties are shown in Table 1, Table 3 and Table 4, respectively.

No difference is recognized between the compounds of Examples and Comparative Examples in connection with their properties, elemental analysis (C,H,N) and infrared spectra in Table 3. However, the melting points of the compounds of Examples 1 to 3 are lower than that of Comparative Example. This fact indicates that while the cis-oxalato(trans-1-1,2-cyclohexanediamine) Pt(II) conventionally obtained is contaminated with such an impurity of its optical isomer, the cis-oxalato(-trans-1-1,2-cyclohexanediamine) Pt(II) obtained in Examples of the present invention is contaminated with no impurities.

Table 4 shows an acute toxicity test ($LD_{60}$) and a resistance against a tumor of L1210 of cis-oxalato(trans-1-1,2-cyclohexanediamine) Pt(II). The test was conducted by prescribing L1210 in a peritoneal cavity of six $CDF_1$ mice/one group (the number of transplanted cells is $10^n$ per mouse and prescribing the medicine in the poritoncal cavity on a first day, a fifth day and a ninth day.

TABLE 1

Optical Purity of Cis-Oxalato(Trans-1-1,2-Cyclohexanediamine) Pt(II)

| Experiment | Raw Material | Optical Purity (e. c. %) | |
|---|---|---|---|
| | | Before Resolution By HPLC → | After Resolution By HPLC |
| Example 1 | Aldrich | 88.5 → | 100 |
| Example 2 | Tokyo Kasei | 90.0 → | 100 |
| Example 3 | Wako Junyaku | 86.8 → | 100 |
| Com. Ex. | Tokyo Kasei | 90.0 → | 100 |

TABLE 2

Angle of Rotation of trans-1-1,2-cyclohexanediamine-(+)-tartaric acid

| Tokyo Kasei (Lot No. FBZ01) | $[\alpha]_n^{10}$ (1% $H_2O$) |
|---|---|
| Before Recrystallization | +12.0+ ± 0.1° |
| After One Recrystallization | +12.1° ± 0.1° |
| After two Recrystallizations | +12.1° ± 0.1° |

TABLE 3

Physicochemical Properties of cis-oxalato(trans1-1,2-cyclohexanediamine)Pt(II)

| Experiment | Melting Point | CD (Δε) | $[\alpha]_n^{20}$ (0.5%, $H_2O$) |
|---|---|---|---|
| Example 1* | 198.3~ | 255 nm | |
| Example 2* | 291.7° C. | +0.67 ± 0.19 | >74.5° C. |
| Example 3* | | 324 nm +0.61 ± 0.10 | |
| Comp. Ex. (JP Publi. No. 60-41077) | >300° C. | not mentioned | not mentioned |

*High Purity Sample Prepared by HPLC

TABLE 4

Acute Toxicity Test and Tumor Resistance Against L1210 of Cis-Oxalato(Trans-1-1,2-cyclohexamediamine) Pt(II)

| Experiment | Acute Toxicity Test $LD_{50}$ | Tumor Resistance T/C (%) (mg/kg) | | | | | |
|---|---|---|---|---|---|---|---|
| | | 25 | 12.5 | 6.25 | 3.12 | 1.56 | 0.78 |
| Example 1* Example 2* Example 3* | 18.2~20.8 mouse IP | T 129P | 280P (2/6) | 311P (3/6) | 207P | 158P | 132P |
| Comp. Ex. | 14.8~19.0 mouse IP | T 81 | 308P (4/6) | 253P (1/6) | 191P | 158P | |

*High Purity Sample Prepared by HPLC
P: Effective (Over 125%)
T: Toxic (Large Weight Loss)
(3/6): This means that three out of six was cured.

What is claimed is:

1. Optically pure cis-oxalato (trans-1-1,2-cyclohexanediamine) Pt(II) having a general formula of Formula (1).

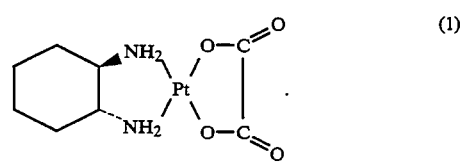

2. Cis-oxalato (trans-1-1,2-cyclohexanediamine) Pt(II) as claimed in claim 1, wherein the melting point thereof is between 198° C. and 292° C.

* * * * *